United States Patent [19]
Helfgott et al.

[11] Patent Number: 4,530,359
[45] Date of Patent: Jul. 23, 1985

[54] OPHTHALMIC PERFORATING INSTRUMENT AND SURGICAL METHOD EMPLOYING SAID INSTRUMENT

[76] Inventors: Maxwell A. Helfgott, 5640 Bradley Blvd., Bethesda, Md. 20814; Gerald N. Helfgott, 5513 Uppingham St., Chevy Chase, Md. 20815

[21] Appl. No.: 464,892

[22] Filed: Feb. 8, 1983

[51] Int. Cl.³ .................................................. A61B 17/34
[52] U.S. Cl. .................................. 128/329 R; 128/305; 30/362
[58] Field of Search ............ 128/329 R, 329 A, 24 A, 128/305, 303.15, 4–8, 314, 315; 112/80, 79.5; 223/102, 104; 30/358, 362, 366; 83/30, 660; 81/9.2, 9.22

[56] References Cited

U.S. PATENT DOCUMENTS

| 2,070,281 | 2/1937 | Leggiadro | 128/305 |
|---|---|---|---|
| 2,112,056 | 3/1938 | Wappler | 128/7 |
| 2,487,498 | 11/1949 | Wallace | 128/7 |
| 2,684,069 | 7/1954 | Donaldson et al. | 128/303 |
| 3,007,471 | 11/1961 | McClure, Jr. | 128/2 |
| 3,410,269 | 11/1968 | Hovick | 128/361 |
| 3,522,809 | 8/1970 | Cornell | 128/305 |
| 3,608,539 | 9/1971 | Miller | 128/2 |
| 3,809,093 | 5/1974 | Abraham | 128/305 |
| 3,888,258 | 6/1975 | Akiyama | 128/305 |
| 3,929,123 | 12/1975 | Jamshidi | 128/2 B |
| 4,002,169 | 1/1977 | Cupler | 128/276 |
| 4,007,732 | 2/1977 | Kvavle et al. | 128/2 B |
| 4,190,041 | 2/1980 | Chikama | 128/4 |
| 4,316,465 | 2/1982 | Dotson | 128/305 X |

FOREIGN PATENT DOCUMENTS

| 257747 | 3/1965 | Australia . | |
|---|---|---|---|
| 3007994 | 9/1980 | Fed. Rep. of Germany . | |
| 8002499 | 11/1980 | Int'l Pat. Inst. | 128/303.15 |
| 1446767 | 8/1976 | United Kingdom . | |
| 149537 | 11/1961 | U.S.S.R. . | |

OTHER PUBLICATIONS

D. Aron-Rosa, "Use of a Pulsed Neodymium-Yag Laser for Anterior Capsulotomy before Extracapsular Cataract Extraction", Am. Intra-Ocular Implant Soc. J., 7:332 (1981).

Primary Examiner—Michael H. Thaler
Attorney, Agent, or Firm—Robbins & Laramie

[57] ABSTRACT

A surgical instrument for ophthalmic use comprises a rigid elongated outer tubular member which terminates in a closed distal end immediately adjoining a distal side opening. A flexible elongated wire is arranged within the outer tubular member and extends in a direction generally parallel to the longitudinal axis of the outer tubular member. The wire is axially movable within the outer tubular member and has a sharp distal end which is positioned in proximity to the distal side opening. The closed distal end of the outer tubular member is provided with an interior curvature which functions as a deflecting member to deflect the distal end of the wire so that the wire projects through the distal side opening at an angle relative to the longitudinal axis of the outer tubular member when the wire is moved axially toward the distal end of the outer tubular member. The wire may be supported by an inner tubular member which is slidable within the outer tubular member and which also functions to conduct an infusion fluid to the instrument tip. Modifications to the basic embodiment include the use of a fixed length of small diameter inner guide tubing as the deflecting member to guide the distal portion of the wire in the direction of the distal side opening in the outer tubular member, and the formation of the wire as a ribbon-like extension of the slidable inner tubular member which serves as the infusion conduit. A surgical method employing the perforating instrument is also disclosed.

28 Claims, 11 Drawing Figures

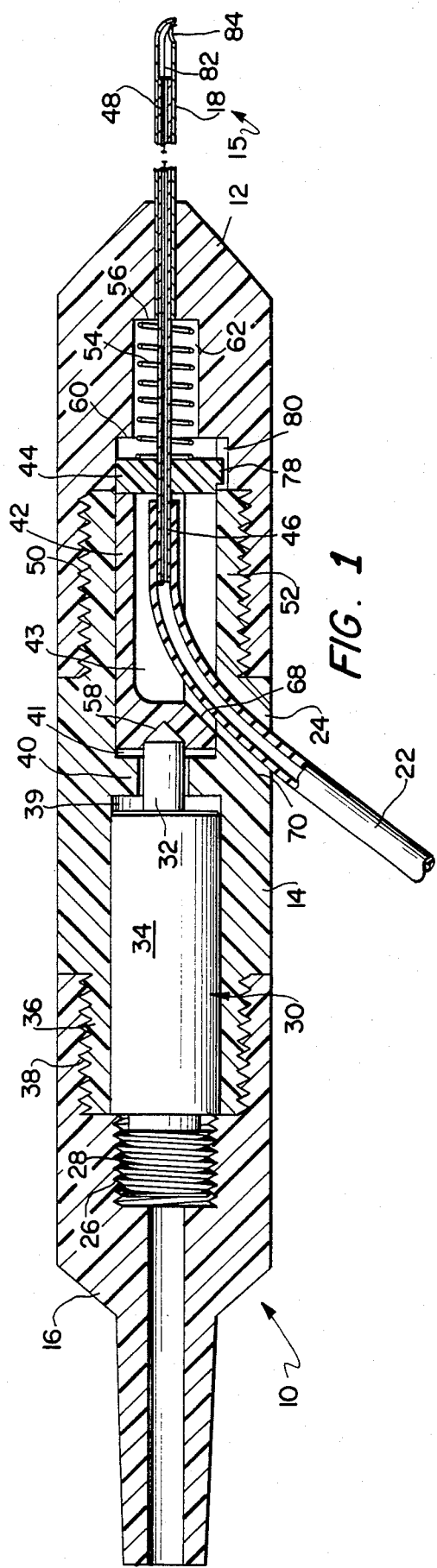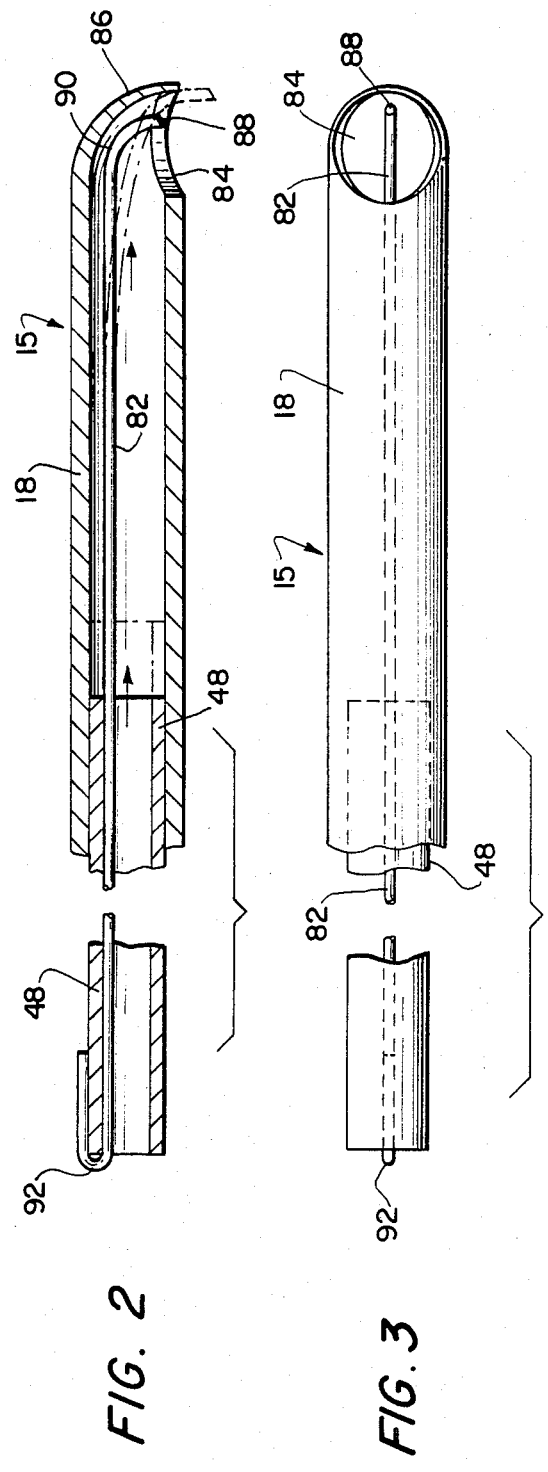

OPHTHALMIC PERFORATING INSTRUMENT AND SURGICAL METHOD EMPLOYING SAID INSTRUMENT

BACKGROUND OF THE INVENTION

1. Field of the Invention

The present invention relates generally to surgical instruments and methods, and is particularly concerned with an ophthalmic instrument and method in which a flexible wire is used to make a line of perforations in the anterior lens capsule of the eye.

2. Description of the Prior Art

Endophthalmic surgery, or surgery on an intact and normally pressurized eye, represents an important and relatively recent development in the field of ophthalmology. In this technique, the existing optical pathways of the pressurized ocular globe are utilized for visualization during delicate intraocular manipulations. Maintenance of positive intraocular pressure tends to preserve and stabilize the spatial relationships among the various intraocular tissues.

The archetypal endophthalmic procedure is the cataract aspiration technique of extracapsular cataract surgery described by Scheie, *Am. J. Ophthal.* 50:1048 (1960), wherein an instrument is passed through a small incision at the margin of the cornea into the anterior aqueous chamber of the eye to incise the anterior capsular membrane of the lens. The aqueous, which leaks out during this manipulation, is replaced by a gravity-fed infusion of physiologic saline through a cannula inserted into the anterior chamber through a second small incision. A blunt needle is then inserted through the first incision into the lens, whereupon gentle suction aspirates the soft lens substance leaving the posterior capsular membrane in place. Whatever volume is removed or leaks from the two small incisions is replaced by the continuous gravity feed of saline. Absent any seepage or applied suction, the pressure in the eye stabilizes at a point determined by the physical elevation of the saline column above the level of the eye. At the end of the procedure, all tubes are withdrawn and the incisions are sutured.

The crystalline lens of the eye is a viscid, cellular, biconvex structure enclosed in a transparent, elastic membrane known as the capsule. The lens adjoins the posterior iris and posterior chamber anteriorly, the zonular ligaments and ciliary body equatorially, and the vitreous body posteriorly. When disease or degeneration degrades the optical quality of the crystalline lens, the resulting opacity is called a cataract. Modern cataract surgery involves removal of either the entire lens and capsule, which is known as intracapsular cataract extraction (ICCE), or piecemeal removal of the lens substance after opening or excising the capsule, which is known as extracapsular cataract extraction (ECCE). Both techniques have undergone steady refinement over the past century in order to reduce the risks and improve the results of cataract surgery.

Modern endophthalmic ECCE requires a controlled, predictable opening in the anterior capsule. Many techniques and instruments have been proposed with which to accomplish this.

The earliest method of opening the anterior capsule was needling or incising the membrane with multiple, slashing incisions made with a knife needle or a scythe-like instrument called a cystotome. Another early technique involved grasping the anterior capsule with tooth forceps and tearing off a piece of the capsule. Of course, because of the large size of the instrument, it was necessary to open the eye in order to maneuver the instrument onto the surface of the capsule.

The precursor of modern capsulectomy techniques is the "Christmas tree" or dull cystotome method as popularized by Kelman. The anterior capsule is engaged opposite the entry site and is torn in one movement toward the surgeon, creating a triangular flap which is pulled out of the eye and then excised. As originally described by Kelman, other small tears could be added along the sides of the triangle to enlarge the opening.

Renewed interest in ECCE in recent years has led to many alternative capsulectomy methods. The common theme has been to increase the control of the excision with less emphasis on tearing and ripping. Also, it is well recognized that endosurgical capsulectomy is particularly desirable in order to visualize the capsule and avoid damage to adjacent intraocular tissues.

One technique suggested the use of a circular resistance wire encased, except for its concave posterior surface, in an insulating disc which would be apposed to the anterior capsule with mild suction. The wire would be briefly heated to cut the membrane. This technique has not become commercially available.

The most widely used capsulectomy technique at the present time is a modification of the "Christmas tree" method, known as the "canopener" method. The instrument used is usually a 25 to 30-gauge hypodermic needle with its bevel bent at 90 degrees to the shaft. This is placed in the eye through a small incision and used to make small triangular tears, which are typically confluent, along the desired line of excision. Although in skilled hands this is an extremely effective method, it is difficult to master for the occasional ECCE surgeon. Another drawback is that the pupil must be widely dilated, since the instrument is controlled by direct visualization. This technique is also very difficult when the capsule is very thick and loose, as in traumatic cataract, or when the capsule is thin and tense, as in a mature or ripe cataract.

There has been at least one attempt to design a powered surgical instrument capable of opening the anterior lens capsule of the eye prior to cataract surgery. In U.S. Pat. No. 3,809,093 to Abraham, a hand-held surgical instrument is described which includes a rod or probe terminating in a small globular tip. An electromagnetic vibrating mechanism in the handle portion of the instrument imparts a limited transverse arcuate or swinging motion to the rod and tip at a controllable rate up to about 100 cycles per second. The globular tip may be provided with a pointed or knife edged projection in order to form multiple incisions in the anterior capsule of the lens as the rod or probe vibrates. With different types of smooth, abrasive or knife-edged globular tips, the instrument can also be used to carry out other types of intraocular surgical procedures, such as cataract disintegration or removal of the posterior lens capsule. The difficulty with this instrument, at least insofar as its application to removal of the anterior lens capsule is concerned, is that the vibration of the globular tip occurs in a direction transverse to the direction of the pointed or knife-edged projection. As a result, the incisions in the anterior lens capsule are actually small rips or tears, rather than discrete perforations. Also, the exposed vibrating tip of this instrument may pose a danger to neighboring intraocular tissues, particularly when it is desired to incise the anterior lens capsule in the marginal region beneath the dilated iris.

More recently, pulsed infrared and near-infrared lasers have been demonstrated to be capable of creating multiple fine perforations of the anterior capsule prior to surgery. This development has been reported by D. Aron-Rosa, *Am. Intra-Ocular Implant Soc. J.* 7:332 (1981). The laser method is advantageous because it requires no direct instrument contact with the lens capsule, and hence it is substantially non-invasive. However, this method requires a clear optical path to the capsule surface and is therefore incapable of forming the desired line of perforations along the marginal portion of the anterior capsule which is obscured by the dilated iris. Another drawback of this technique is that the necessary laser equipment is extremely large and extraordinarily expensive, and accomplished essentially the same result that can be obtained by using a disposable hypodermic needle.

In summary, the evolution of eye surgery in general and ECCE in particular is characterized by emphasis on precise placement of all tissue handling instruments, controlled incisions rather than unpredictable ripping or tearing, and the use of endosurgical techniques allowing microscopic visualization using the intact optical pathways of the eye.

SUMMARY OF THE INVENTION

In accordance with the present invention, the foregoing disadvantages and limitations of the prior art are substantially avoided by providing an ophthalmic surgical instrument which comprises a rigid elongated outer tubular member terminating in a closed distal end immediately adjoining a distal side opening. A flexible elongated wire is arranged within the outer tubular member and extends in a direction generally parallel to the longitudinal axis of the outer tubular member. The wire is axially movable within the outer tubular member and has a sharp distal end which is positioned in proximity to the distal side opening formed in the outer tubular member. Deflecting means within the closed distal end of the outer tubular member is effective to deflect the distal end of the wire so that the wire projects through the distal side opening at an angle relative to the longitudinal axis of the outer tubular member in response to axial movement of the wire toward the distal end of the outer tubular member. The deflecting means may comprise a distal end wall on the outer tubular member which has a curved interior surface, or a rigid small diameter inner guide tube, preferably curved, which is affixed within the outer tubular member in surrounding relationship with the distal end of the wire. In a preferred embodiment of the invention, the wire is supported by an inner tubular member which is coaxially and slidably arranged within the outer tubular member, with the inner tubular member serving as an infusion line for conducting fluids to the instrument tip. In this embodiment, the wire may comprise a ribbon-like extension of the inner tubular member itself, although it is also possible to employ a separate wire which is attached by any suitable method to the inner tubular member.

In operation, the instrument is inserted through a limbal incision made at the margin of the cornea. The tip of the instrument is positioned so that the distal side opening in the outer tubular member faces the anterior lens capsule at the point where the desired perforations are to be made. The wire is then reciprocated back and forth in an axial direction within the outer tubular member, causing the sharpened distal end of the wire to repeatedly project from the distal side opening and to perforate the capsular membrane. After each perforation is made, the instrument tip may be moved slightly to create a further perforation located very close to the preceeding perforation. This process may be repeated until a continuous line of perforations has been defined around the margin of the capsular membrane. The finished line of perforations defines a weakened tear or score line which will allow the central portion of the anterior capsule to be pulled back or removed in order to provide access to the lens material for cataract removal or the like. Saline infusion may be introduced through the instrument tip, preferably by means of the slidable inner tubular member which carries the flexible wire, in order to replace any lost aqueous and prevent collapse of the cornea.

The present invention provides a number of important advantages over previously used techniques for opening the anterior lens capsule. In the first place, the sharpened tip of the wire which projects from the distal side opening of the instrument forms a clean perforation in the capsular membrane, without any significant amount of ripping or tearing. Since the perforations are non-confluent, unlike the triangular incisions resulting from the prior art "can opener" method, the tautness of the capsular membrane is preserved as the perforations are formed. Both of these factors, that is, the lack of ripping or tearing in the perforations and the preservation of the tautness of the capsular membrane, are helpful in providing a controlled, predictable opening in the anterior capsule. In addition, since there is no movement at the instrument tip other than the protusion of the wire through the distal side opening, the instrument can be used without the risk of damage to tissues adjoining the anterior capsule. Finally, unlike the laser method, there is no requirement for a clear optical path to the area of the anterior capsule where the perforations are to be made. This permits the line of perforations to be defined around the marginal portion of the anterior capsule which is obscured by the dilated iris, and hence allows a relatively large opening to be made in the anterior capsule.

The present invention also embraces a surgical method for opening an intraocular lens capsule which can be carried out using the instrument described above. The method involves the steps of repeatedly penetrating the lens capsule with the sharpened tip of a flexible wire or ribbon without appreciable ripping or tearing of the capsule to form a line of closely spaced, non-confluent perforations in the lens capsule, and then pulling away or removing a portion of the lens capsule along the line of perforations. The line of perforations may extend completely around the surface of the lens capsule, as for example where it is desired to completely remove or excise a portion of the lens capsule. Alternatively, the line of perforations may extend only partially around the surface of the lens capsule, as for example where it is desired to create a capsule flap which can be pulled away from the adjoining portion of the lens capsule. In order to create the largest possible opening in the lens capsule, the line of perforations preferably extends at least partially beneath the iris of the eye. A saline infusion is preferably conducted into the eye during the forming of the perforations in order to maintain positive intraocular pressure. The method is especially useful for opening the anterior lens capsule of the eye, but can also be used to remove the posterior lens capsule if desired.

BRIEF DESCRIPTION OF THE DRAWINGS

The various objects, advantages and novel features of the present invention will be more readily apprehended from the following detailed description when read in connection with the appended drawings in which:

FIG. 1 is a side sectional view of powered surgical handpiece which is fitted with one embodiment of the perforating instrument of the present invention;

FIG. 2 is an enlarged side sectional view of the perforating instrument, with portions of the inner and outer tubular members omitted for clarity;

FIG. 3 is an enlarged bottom view of the perforating instrument, also with portions of the inner and outer tubular members omitted;

Throughout the drawings, like reference numerals are used to identify like parts.

Figure 4:
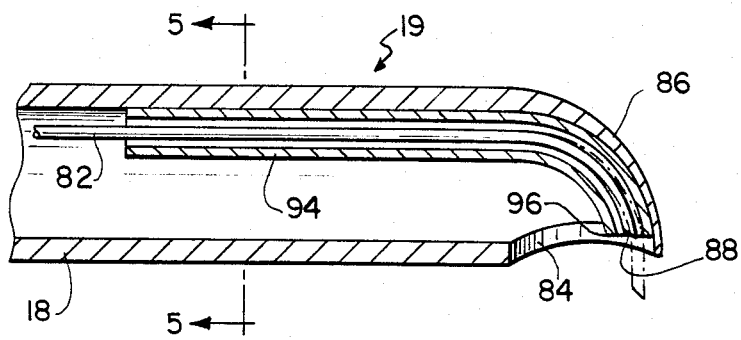
FIG. 4 is an enlarged side sectional view of the distal portion of a perforating instrument constructed in accordance with a second embodiment of the present invention.

DETAILED DESCRIPTION OF THE PREFERRED EMBODIMENTS:

FIG. 1 is a side sectional view of a powered surgical handpiece 10 which may be fitted with the perforating instrument of the present invention. The handpiece 10 is described in detail in the applicants' earlier U.S. Pat. No. 4,314,560, which patent is expressly incorporated herein by reference.

The handpiece 10 will be seen to include a cylindrical housing comprising an anterior cylindrical section 12, a central cylindrical section 14, and a rear cylindrical section 16. The rear part of the central housing section 14 includes an externally threaded portion 36 which engages a corresponding internally threaded portion 38 of the rear housing section 16. In a similar manner, the forward end 52 of the central housing section 14 is externally threaded in order to engage a corresponding internally threaded portion 50 of the anterior housing section 12. The central section 14 and rear section 16 together comprise what may be referred to as the posterior section of the handpiece or, in connection with the components they receive, as the main body of the handpiece.

The anterior section 12 of the handpiece is fitted with a projecting tubular surgical instrument 15 which includes an elongated outer tubular member 18 and an inner tubular member 48. The inner tubular member 48 is coaxially and slidably received within the outer tubular member 18 for axial reciprocation therein. A flexible wire 82 is carried by the inner tubular member 48 and extends generally parallel to the longitudinal axis of the outer tubular member 18. The distal end of the wire 82 is positioned in proximity to a distal side opening 84 formed in the outer tubular member 18 and projects a short distance through the opening 84 when the handpiece 10 is in operation. The structure and operation of the instrument 15, together with alternative embodiments thereof, is the subject matter of the present invention and will be described in some detail hereinafter.

A flexible pneumatic supply line, not shown, is attached to the rear section 16 of the handpiece 10 and is connected at its opposite end to a suitable pneumatic power supply, also not shown, for providing intermittent pulses of compressed air or other gas to a pneumatic actuator 30 within the handpiece. The pneumatic actuator 30 imparts axial reciprocating motion to the inner tubular member 48 within the fixed outer tubular member 18, the latter being press-fitted into the anterior section 12 of the handpiece. A flexible tube 22 is connected at a point within the handpiece to the proximal end of the inner tubular member 48, as shown, and passes loosely out of the handpiece through an opening 24 formed in the cylindrical side surface of the handpiece. The inclined rear wall portion 70 of the opening 24 and the inclined guide surface 68 formed on the closed end portion 66 of a coupling member 42 cooperate to assist the flexible tube 22 in bending smoothly as it passes out of the handpiece. The flexible tube 22 will normally be used for conducting infusion fluids through the inner tubular member 48 when the projecting surgical instrument is of the type shown, although for other types of instruments the flexible tube 22 may be used to apply suction (aspiration) to the inner tubular member. In this connection, it should be noted that the anterior portion 12 of the handpiece is removable to permit the attachment of different types of surgical instruments, a capability which will become more apparent as the description proceeds.

With continued reference to FIG. 1, the coupled rear section 16 and central section 14 of the handpiece housing together define an internal cylindrical cavity 39 for receiving the pneumatic actuator 30. The rear section 16 of the housing is provided with internal threads 26 for making airtight engagement with a threaded fitting 28 formed on the rear part of the pneumatic actuator 30. The pneumatic actuator 30 contains an internal piston and spring return for urging a pusher member 32 linearly or axially outward with respect to the cylindrical body portion 34 of the actuator in response to the intermittent pneumatic pressure pulses supplied through the fitting 28. An annular wall 40 located a short distance behind the opening 24 in the central housing section 14 defines the forward extent of the cavity 39 and provides a circular aperture through which the pusher member 32 passes. The conical tip of the pusher member 32 is received in a correspondingly shaped depression 58 formed in one end of the coupling member 42.

The coupling member 42 is slidably received in a cylindrical cavity 41 located forward of the annular wall 40 and serves to transmit the axial reciprocating motion of the pusher member 32 to a disk-shaped platform member 44. The platform member 44 is secured to the inner tubular member 48 of the surgical instrument at a point somewhat ahead of the proximal end of the inner tube 48, thereby insuring sufficient room for the attachment of the flexible tube 22 to the inner tube 48. The platform member 44 is maintained in abutting contact with the forward part of the coupling member 42 by virtue of a return spring 54. The return spring 54 is confined within a narrow cylindrical cavity 62 formed within the anterior section 12 of the handpiece, and is maintained in a compressed condition between the platform member 44 and the forward interior wall 56 of the cavity 62.

In operation, the coupling member 42 provides an abutting mechanical connection between the reciprocating pusher member 32 of the pneumatic actuator 30 and the platform member 44 which is secured to the proximal end 46 of the inner tubular member 48. At the same time, the recessed configuration of the coupling member 42 resulting from the open cavity 43 formed therein permits the flexible tube 22 to be connected to the proximal end 46 of the inner tubular member 48 as the latter reciprocates. Such reciprocation will occur when a positive pressure pulse is applied to the pneumatic actuator 30, causing the pusher member 32 to move forward. This forward motion is transmitted by the coupling member 42 to the platform member 44, which moves forward to the limit of its travel as defined by the annular shoulder 60. The forward motion of the platform member 44 causes an equal forward movement of the inner tubular member 48 and wire 82 within the outer tubular member 18, which causes the distal tip of the wire to protrude from opening 84 at the instrument tip. This produces a tissue perforating action at the instrument tip as will be described hereinafter. When the pressure pulse terminates, the pusher member 32 retracts and the return spring 54 causes the platform member 44 and coupling member 42 to return to their rest positions. This motion retracts the inner tubular member 48 and wire 82 and completes the cycle of operation. The platform member 44 is provided with a projecting key 78 for engaging a corresponding longitudinal groove 80 formed on the interior surface of the anterior housing section 12. The purpose of this arrangement is to maintain the inner tubular member 48 in a fixed rotational position with respect to the outer tubular member 18.

The handpiece 10 of FIG. 1 allows interchangeability among different surgical instruments simply by uncoupling the anterior housing section 12 from the main body of the handpiece. This allows the removal of the inner and outer tubular members 48, 18 and the wire 82, which form the surgical instrument 15, together with the return spring 54, the platform member 44, and the anterior housing section 12 which carries all of these components. Such removal is readily accomplished in view of the fact that there is no necessity for rigid mechanical connection between the coupling member 42 and the platform member 44 when the handpiece is in its assembled condition, since the return spring 54 maintains these components in abutting contact with each other. When the anterior housing section 12 is removed, the platform member 44 and the coupling member 42 are separated, with the coupling member 42 remaining behind as part of the main body of the handpiece. A new anterior housing section, carrying a different type of surgical instrument (or the same type of instrument in cases where the previous instrument has simply become worn), as well as a new platform member and return spring, can now be coupled to the main body of the handpiece. The necessity of threading the flexible tube 22 through the opening 24 in the side of the handpiece during the substitution of a new instrument can be avoided by extending the opening 24 to the forward edge of the central housing section 14 to form an open-ended slot. When the anterior housing section 12 has been attached, its rear edge closes off the open end of the slot to form the functional equivalent of the opening 24.

The surgical instrument 15 is illustrated in more detail in the enlarged views of FIGS. 2 and 3. The instrument 15 includes a rigid elongated outer tubular member 18, circular in cross-section, which terminates in a closed distal end wall 86 immediately adjoining a distal side opening 84. The distal end wall 86 is curved to provide an interior curvature within the distal end of the outer tubular member 18. A rigid inner tubular member 48, also circular in cross-section, is coaxially and slidably arranged within the outer tubular member 18 with its open distal end terminating well behind the side opening 84 in the outer tubular member as shown. The inner tubular member 48 carries a flexible elongated wire 82 which is arranged within the outer tubular member 18 so that the wire extends generally parallel to the longitudinal axis of the outer tubular member. The wire 82 is provided with a sharpened distal tip 88 which is positioned in proximity to the distal side opening 84 formed in the outer tubular member 18. The flexible wire 82 is preferably pre-formed with its distal end portion 90 curved in the direction of the side opening 84, as shown. The proximal portion of the wire 82 runs parallel to, and is in contact with, the interior side wall of the inner tubular member 48, and terminates in a U-shaped bend 92 at the open proximal end of the inner tubular member. The exposed portion of the wire 82 is secured to the proximal outside surface of the inner tubular member 48 by any suitable method, such as soldering or brazing. This method of exterior attachment leaves the interior of the inner tubular member 48 open and unobstructed so that it can be used for infusion purposes as will be described shortly.

The operation of the instrument 15 may be readily understood with reference to FIG. 2. When the inner tubular member 48 is in the retracted position, shown in solid outlines in FIG. 2, the sharpened distal tip 88 of the wire 82 is positioned just inside the distal side opening 84 of the outer tubular member 18. These are the positions of the wire 82 and inner tubular member 48 when no pressure pulse is applied to the pneumatic actuator 30 of the handpiece 10 in FIG. 1. During an operating stroke, the application of a positive pressure pulse to the pneumatic actuator 30 causes the inner tubular member 48 to slide forward to the phantom line position shown in FIG. 2. When this occurs, the distal portion 90 of the wire 82 is brought into contact with the closed distal end 86 of the outer tubular member 18. The interior curvature of the distal end wall 86 serves as a deflecting member and is effective to deflect the distal end of the wire 82 so that the sharpened tip 88 projects through the distal side opening 84 at an angle of about 90° relative to the longitudinal axis of the outer tubular member 18. This is illustrated by the phantom line position of the wire 82 in FIG. 2. The projecting tip 88 of the wire will serve to form a hole or perforation in the anterior lens capsule or other intraocular tissue positioned below the distal side opening 84. When the pressure pulse to the pneumatic actuator 30 of FIG. 1 terminates, the inner tubular member 48 and the wire 82 return to the solid line positions shown in FIG. 1, and the sharpened tip 88 of the wire 82 is once again retracted to a position just inside the distal side opening 84 of the outer tubular member 18. This completes one cycle of operation. It should be noted that, since the movement of the sharpened tip 88 of the wire 82 occurs roughly in the direction in which the sharpened tip 88 initially points, the instrument 15 will be capable of creating a distinct hole or perforation in the intraocular tissue with a minimum of ripping or tearing.

A saline infusion is preferably conducted through the inner tubular member 48 by virtue of the flexible infusion tube 22 of FIG. 1 in order to maintain normal intraocular pressure when the instrument 15 is being used. The saline infusion exits from the side opening 84 at the distal end of the outer tubular member 18, and it is for this reason that the side opening 84 is somewhat larger than necessary for free movement of the distal tip 88 of the wire 82. If desired, however, the opening 84 may be made smaller and one or more further openings may be provided in the anterior side wall of the outer tubular member 18 to assure an unobstructed outflow of the infusion fluid.

In practice, the instrument 15 may be fabricated by using surgical-quality stainless steel hypodermic tubing for the inner and outer tubular members 48 and 18. The outer tubular member 18 may comprise 20-gauge T-304 stainless steel with a wall thickness of 0.006 inch. The inner tubular member 48 may comprise 23.5-gauge tubing of the same material with a 0.003-inch wall thickness. In order to provide the distal end 86 of the outer tubular member 18 with the configuration illustrated in FIG. 2, the outer tube 18 may be bent sharply through an angle of 90° and then cut at the point of bending to form the distal side opening 84. The curved distal end surface 86 of the outer tubular member 18 corresponds to the outer radius of the bend prior to cutting. The natural tendency of the tubing to stretch at the outer radius of the bend accounts for the reduced thickness of the distal end surface 86 where it adjoins the side opening 84. The flexible wire 82 may be made of a single 0.004-inch diameter strand of stainless steel, beveled at its distal end to form the sharpened tip 88. The proximal end of the wire 82 is secured to the open proximal end of the inner tubular member 48 by soldering or brazing in the manner described previously. The distal portion 90 of the wire 82 is preferably curved through a gradual arc, as shown, so that the tip 88 of the wire aligns with the distal side opening 84 of the outer tubular member 18. This tends to assist the curved distal end surface 86 of the outer tubular member 18 in deflecting the distal end of the wire 82 so that it can project smoothly from the distal side opening 84 without becoming caught or lodged within the instrument tip. Also, the curvature at the distal end of the wire 82 forces the wire to project from the distal side opening 84 in a direction more nearly normal to the longitudinal axis of the outer tubular member 18 than would otherwise be the case.

It should be understood that the foregoing dimensions and specifications, together with any dimensions and specifications given hereinafter, are presented merely by way of example and are not intended to limit the scope of the present invention in any way, except as defined in the appended claims.

Ideally, it is desirable for the distal tip 88 of the wire 82 to emerge from the distal side opening 84 in the outer tubular member 18 in a direction very nearly normal to the longitudinal axis of the outer tubular member. This will occur when the distal part of the wire 82 deflects through an angle of 90° as it projects from the distal side opening 84. It is also desirable that the extension of the wire not be accompanied by any sidewise motion of the wire in a direction transverse to the axis of the tip 88. When these conditions are satisfied, perforation of the lens capsule occurs at a highly predictable position beneath the distal side opening 84, and there is a minimum of ripping or tearing since the sharpened tip 88 of the wire penetrates the lens capsule in a vertical or normal direction without any sidewise displacement. The instrument 15 of FIGS. 1 and 2 achieves a roughly perpendiulcar extension of the tip 88 of the wire 82, at least when the amount of extension is small relative to the length of the curved distal portion 90 of the wire. However, the downward extension of the tip 88 of the wire is accompanied by a significant forward displacement of the tip in the right-hand direction, as can be seen by comparing the solid line and phantom line positions of the wire in FIG. 2. This results from the tendency of the straight portion of the wire behind the curved distal portion 90 to slope slightly downward as the wire is forced against the curved distal end 86 of the outer tubular member 18, which brings the forward edge of the distal opening 84 into contact with a point slightly higher on the curved distal end 90 of the wire.

Figure 5:
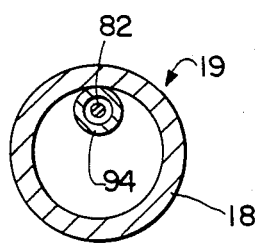
FIG. 5 is a cross-sectional view taken along the line 5—5 in FIG. 4.

FIGS. 4 and 5 illustrate a modification of the surgical instrument which is effective to avoid the problem referred to above. The surgical instrument 19 of FIGS. 4 and 5 is in most respects the same as the instrument 15 of FIGS. 2 and 3, except that the modified instrument 19 has been provided with a rigid length of small diameter inner guide tubing 94 affixed within the outer tubular member 18 near the distal end thereof. The guide tube 94, which may be made from a length of 29-gauge stainless steel tubing, is open at both ends and is affixed by welding or the like along the interior wall of the outer tubular member 18. The open distal end 96 of the guide tube 94 is positioned within the side opening 84 of the outer tubular member 18 and points in a direction approximately normal to the longitudinal axis of the outer tubular member 18. The guide tube 94 is curved lengthwise through an arc of about 90° to match the curvature of the closed distal end 86 of the outer tubular member 18, and has its open proximal end 97 positioned in the interior of the outer tubular member 18 and pointing in a direction approximately parallel to the longitudinal axis of the outer tubular member 18. The flexible wire 82 is threaded through the guide tube 94 so that the latter completely surrounds the curved distal portion of the wire which terminates in the sharpened tip 88.

In the embodiment of FIGS. 4 and 5, the deflection of the distal end of the wire 82 as it projects through the side opening 84 is caused by the curvature of the guide tube 94, rather than by the curved interior surface of the distal end 86 of the outer turbular member 18. Since the path of the distal part of the wire is constrained to follow the contour of the guide tube 94, the projection of the sharpened tip 88 of the wire from the distal side opening 84 of the instrument occurs in a direction very nearly normal to the longitudinal axis of the outer tubular member 18, as indicated by the dotted line position in FIG. 4. This is not accompanied by any appreciable forward movement of the wire in a direction transverse to the axis of the tip 88, since the upper proximal portion of the guide tube 94 prevents any deviation of the straight proximal part of the wire 82 from its horizontal path. This insures that the sharpened tip 88 of the wire will cleanly penetrate the anterior lens capsule in a vertical direction without any appreciable amount of transverse forward movement resulting in ripping or tearing.

Figure 8:
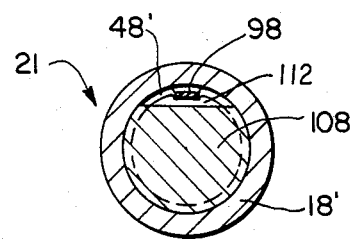
FIG. 8 is a cross-sectional view taken along the line 8—8 in FIG. 6.
Figure 6:
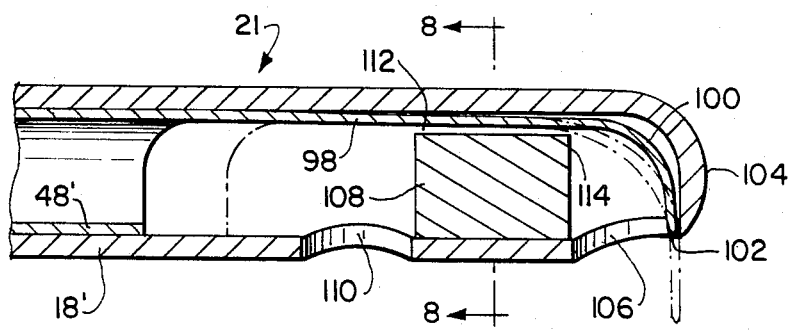
FIG. 6 is an enlarged sectional view of the distal portion of a perforating instrument constructed in accordance with a third embodiment of the present invention.
Figure 7:
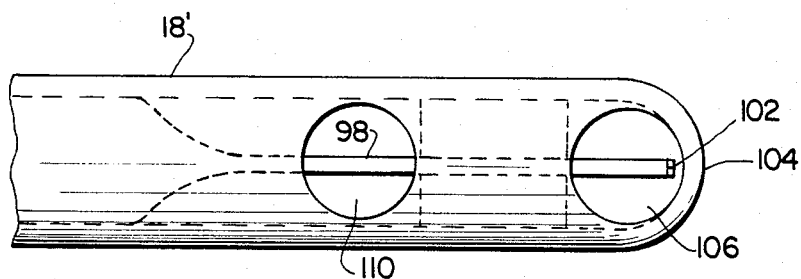
FIG. 7 is a bottom view of the distal instrument portion illustrated in FIG. 6.
Figure 9:
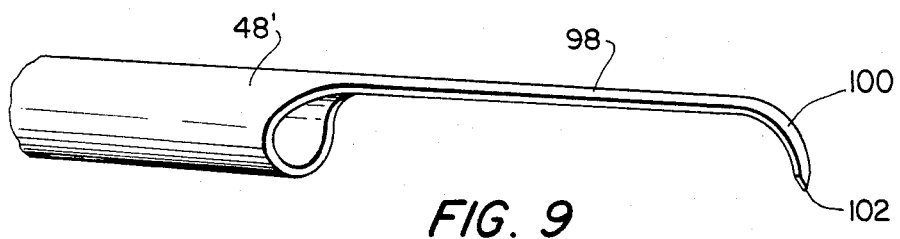
FIG. 9 is a perspective view of the inner tubular member used in the embodiment of FIGS. 6-8, illustrating the ribbon-like extension of the inner tubular member.

In FIGS. 6-9, a further embodiment 21 of the invention is illustrated in which the separate wire 82 of the previous embodiments is replaced by a flexible ribbon-like extension 98 of the inner tubular member 48'. The configuration of the inner tubular member 48' and its ribbon extension 98 can be seen most clearly in FIG. 9, which illustrates the distal portion of the inner tubular member 48' removed from the outer tubular member 18'. The distal end 100 of the ribbon extension 98 is preferably curved through an angle of about 90°, as shown, and the distal tip of the curved portion 100 is provided with a double bevel to form a sharpened point 102. The outer tubular member 18', visible in FIGS. 6-8, is circular in cross-section and formed from a length of cylindrical tubing which terminates in a curved distal end wall 104 having essentially the same wall thickness as the elongated portion of the tube. The distal end wall 104 is essentially hemispherical and adjoins the distal side opening 106 in a manner such that the interior surface of the wall 104 merges smoothly with the forward edge of the side opening 106. Hypodermic tubing incorporating the hemispherical end wall 104, which is referred to as a controlled closure, is commercially available and can be adapted to the present invention simply by forming the distal side opening 106 through a portion of the hemispherical tip.

The operation of the instrument 21 of FIGS. 6-9 is substantially the same as that of the previous embodiments, except that the ribbon extension 98 is somewhat stiffer and more resistant to crimping or buckling within the instrument than the wire 82 of the previous instruments. The stiffness of the ribbon extension 98 also reduces its tendency to deviate or "wander" from side to side as it projects from the instrument tip, which can sometimes be a problem with the wire 82. Finally, the difficulties involved in attaching the wire 82 to the inner tubular member 18 in the previous embodiments are avoided since the ribbon extension 98 is an integral part of the inner tubular member 48'.

In operation, forward movement of the inner tubular member 48' to the phantom line position of FIG. 6 causes the distal end 100 of the ribbon extension 98 to be urged into contact with the curved interior surface of the distal end 104 of the outer tubular member 18'. The interior curvature of the distal end wall 104 causes the sharpened tip 102 of the ribbon extension to project from the distal side opening 106 at an angle of about 90° with respect to the longitudinal axis of the outer tubular member 18'. This position of the tip 102 is illustrated in phantom lines in FIG. 6. As with the embodiment of FIGS. 2 and 3, there is some tendency for the distal tip 102 of the ribbon extension 98 to move forward when this occurs, due to the downward sloping of the proximal part of the ribbon extension 98 which allows the forward edge of the distal side opening 106 to engage a slightly higher point on the curved distal end 100 of the ribbons extension. This effect can be minimized by positioning a guide block 108 within the interior of the outer tubular member 18' at a position immediately behind the distal side opening 106. As can be seen by comparing FIGS. 6 and 8, the guide block 108 comprises a solid cylinder with a narrow longitudinal section removed along one of its edges. The guide block 108 is made of metal or plastic and is affixed to the interior side wall of the outer tubular member 18' in a manner such that the upper planar region of the guide block faces the ribbon extension 98, which runs along the upper side wall of the outer tubular member 18'. In this position, the guide block 108 defines a narrow guide channel 112 for the ribbon extension 98 with respect to the upper side wall of the outer tubular member 18'. When the ribbon extension 98 is moved forward by the inner tubular member 48', the forward edge 114 of the guide block 108 acts as a support for the distal portion 100 of the ribbon extension and reduces the amount of downward sloping which may occur in the proximal region of the ribbon extension 98. As a result, the sharpened tip 102 of the ribbon extension projects from the distal side opening 106 in a direction very nearly normal to the longitudinal axis of the outer tubular member 18, as indicated by the phantom line position in FIG. 6, but does not move forward to any significant extent in the direction transverse to the axis of the tip 102. As pointed out earlier, this is helpful in producing clean perforations in the anterior lens capsule with a minimum of ripping or tearing.

As in the previous embodiments, the inner tubular member 48' of the perforating instrument 21 is preferably used to conduct a saline infusion through the instrument tip in order to maintain normal intraocular pressure during the surgical procedure. With the guide block 108 on place, it will be seen that the flow path which exists between the open proximal end of the inner tubular member 48' and the distal side opening 106 in the outer tubular member 18' is substantially obstructed, except for the narrow guide channel 112 through which the ribbon extension 98 passes. In order to insure an efficient outflow of the infusion fluid from the instrument tip, a second side opening 110 is provided in the side wall of the outer tubular member 18'. The side opening 110 occupies a position between the guide block 108 and the open distal end of the inner tubular member 48'.

Figure 10:
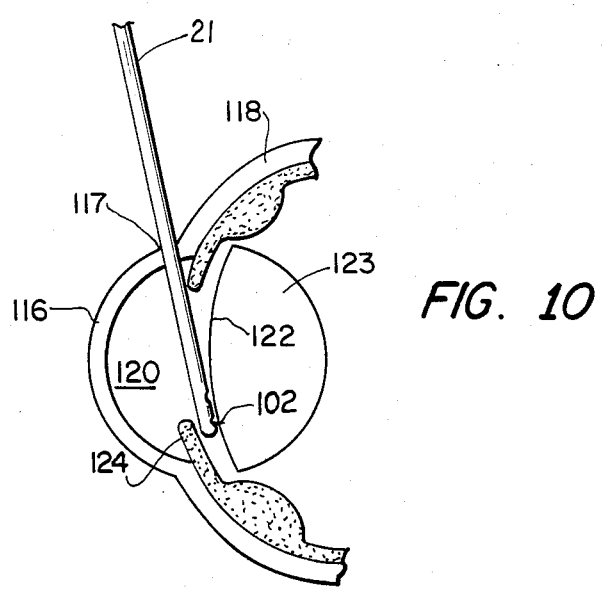
FIG. 10 is a sectional view of the anterior part of the human eye illustrating the insertion of the perforating instrument into the anterior chamber through an incision made at the margin of the cornea.
Figure 11:
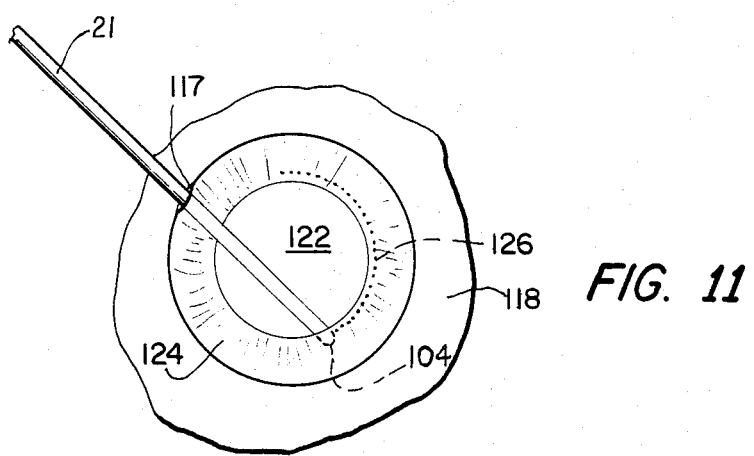
FIG. 11 is an elevational view illustrating the manner in which the perforating instrument of the present invention may be used to define a line of perforations around the margin of the anterior lens capsule of the eye in the area beneath the dilated iris.

FIGS. 10 and 11 illustrate the manner in which the instrument of the present invention may be used to facilitate removal of a portion of the anterior lens capsule of the eye prior to cataract surgery. The instrument 21 which is shown in FIGS. 10 and 11 corresponds to the embodiment of FIGS. 6-9, although it should be understood that the instruments 15 and 19 of FIGS. 2-3 and 4-5, respectively, would be employed in a similar manner. As can be seen most clearly in FIG. 10, the instrument 21 is inserted through a limbal incision 117 which is formed in the marginal part of the cornea 116 at the point where the cornea joins the sclera 118. The instrument tip is maneuvered so that the distal side opening 106 and the retracted tip 102 of the ribbon extension face the anterior capsule 122 of the lens body 123. The instrument tip is preferably positioned in the area behind the dilated iris 124, as shown, so that perforations can be made as close as possible to the margin of the anterior capsule 122.

With the instrument 21 in position, the handpiece 10 of FIG. 1 is operated to cause the sharpened tip 102 of the ribbon within the instrument to protrude from the distal opening 106. The handpiece 10 has been omitted from FIGS. 10 and 11 for clarity. Each time that the sharpened tip 102 of the ribbon projects from the instrument tip, a perforation is made through the anterior capsule 122. The instrument is repositioned by the surgeon after each perforation is made, so that a further perforation can be formed very close to the preceding one. By repeating this process many times, a continuous line of closely-spaced, non-confluent perforations 126 can be formed around the margin of the anterior capsule 122 as illustrated in FIG. 11. Since the perforations are non-confluent, unlike the triangular incisions that are typically made with the prior art "can opener" method, the tautness of the capsular membrane is preserved throughout the perforating step. Also, since the perforations 126 are made without ripping or tearing, the shape of the excision can be carefully controlled. The line of perforations 126 can be made in a complete circle around the surface of the capsular membrane, as where it is desired to completely remove the central port of the anterior capsule. Alternatively, the line of perforations can extend only part way around the surface of the anterior capsule to create a capsule flap. The flap is pulled away from the adjoining portion of the lens capsule but remains partly attached. The latter procedure will be followed, for example, in cases where it is desired to use the capsule flap to secure an ophthalmic lens implant after the surgery has been completed. In either case, the finished line of perforations will define a weakened tear or score line which will allow the central portion of the anterior capsule to be removed or folded back. Access may then be had to the lens material so that further surgical procedures can be formed, such as disintegration and removal of a cataract. When these procedures are completed, all instruments are removed and the incision 117 is sutured.

The handpiece 10 of FIG. 1 may be operated in a single-pulse or slow automatic mode in order to allow the perforations 126 to be made one at a time, with the interval between successive operating cycles being used to reposition the instrument tip at the location of the next desired perforation. Infusion provided through the instrument tip via the flexible tube 22 of the handpiece 10 maintains positive intraocular pressure within the anterior chamber 120 of the eye during the time that the perforations are formed and prevents collapse of the cornea 116.

Although the present invention has been described with reference to specific preferred embodiments, the scope of the invention is not limited to the details thereof. Various substitutions and modifications have been suggested in the foregoing description, and others will occur to those of ordinary skill in the art. All such substitutions and modifications are intended to be embraced within the scope of the appended claims.

What is claimed is:

1. An ophthalmic surgical instrument comprising a rigid elongated outer tubular member terminating in a distal end wall immediately adjoining a distal side opening; and a flexible elongated wire arranged within said outer tubular member and extending generally parallel to the longitudinal axis of said outer tubular member, said wire being axially movable within said outer tubular member and having its distal end positioned in proximity to the distal side opening in said outer tubular member, the distal end of said wire being formed with a single sharp distal tip adapted to form a discrete perforation in intraocular tissues; the distal end wall of the outer tubular member having a curved interior surface for deflecting the distal end of said wire so that the sharp distal tip of said wire projects through said distal side opening at an angle of about 90° relative to the longitudinal axis of the outer tubular member in response to axial movement of said wire toward the distal end of said outer tubular member.

2. An ophthalmic surgical instrument as claimed in claim 1, further comprising means slidable within said outer tubular member for supporting and imparting axial movement to said wire.

3. An ophthalmic surgical instrument as claimed in claim 2, wherein said slidable means comprises an inner tubular member coaxially and slidably arranged within said outer tubular member.

4. An ophthalmic surgical instrument as claimed in claim 3, wherein said outer tubular member is open at its proximal end, and wherein said inner tubular member has an open proximal end which extends beyond the open proximal end of the outer tubular member and an open distal end which terminates within said outer tubular member at a point behind the distal side opening thereof.

5. An ophthalmic surgical instrument as claimed in claim 3, wherein said wire comprises a flexible ribbon-like extension of said inner tubular member.

6. An ophthalmic surgical instrument as claimed in claim 5, wherein the distal end of said ribbon-like extension is curved in the direction of the distal side opening in the outer tubular member.

7. An ophthalmic surgical instrument as claimed in claim 5, wherein said outer tubular member is open at its proximal end, and wherein said inner tubular member has an open proximal end which extends beyond the open proximal end of the outer tubular member and an open distal end which terminates in said ribbon-like extension at a point within said outer tubular member and behind the distal side opening thereof.

8. An ophthalmic surgical instrument as claimed in claim 7, further comprising a guide member affixed to the interior side wall of the outer tubular member at a position immediately behind the distal side opening therein, said guide member defining a narrow channel for guiding the movement of the ribbon-like extension in the vicinity of the distal side opening.

9. An ophthalmic surgical instrument as claimed in claim 8, wherein said guide member comprises a solid guide block, and wherein said channel is defined between an outer face of the guide block and the interior side wall of the outer tubular member.

10. An ophthalmic surgical instrument as claimed in claim 9, wherein said inner and outer tubular members are each circular in cross-section, and wherein said guide block comprises a solid cylinder with a narrow longitudinal section removed along one edge thereof.

11. An ophthalmic surgical instrument as claimed in claim 8, wherein said outer tubular member is provided with a second side opening spaced from said distal side opening and occupying a position between said guide member and the open distal end of said inner tubular member.

12. An ophthalmic surgical instrument as claimed in claim 4, wherein the distal end of the ribbon-like extension which extends beyond the channel defined by said guide member is curved in the direction of the distal side opening in the outer tubular member.

13. An ophthalmic surgical instrument as claimed in claim 1, wherein the distal end of said wire is curved in the direction of the distal side opening in the outer tubular member.

14. In an ophthalmic surgical apparatus comprising a handpiece portion and an instrument portion, said instrument portion comprising rigid inner and outer tubular members with the inner tubular member axially slidable within the outer tubular member, and said handpiece portion comprising power-operated means for axially reciprocating said inner tubular member within said outer tubular member to produce a desired function at the instrument tip, the improved instrument portion comprising: an outer tubular member terminating in a closed distal end immediately adjoining a distal side opening; an inner tubular member having an open distal end which terminates within said outer tubular member at a point behind said distal side opening; a flexible elongated wire arranged within said outer tubular member and carried by said inner tubular member, said wire extending generally parallel to the longitudinal axis of said outer tubular member and having its distal end positioned in proximity to the distal side opening in said outer tubular member, the distal end of said wire being formed with a single sharp distal tip adapted to form a discrete perforation in intraocular tissues; and means within the closed distal end of the outer tubular member for deflecting the distal end of said wire so that the sharp distal tip of said wire projects through said distal side opening at an angle relative to the longitudinal axis of the outer tubular member in response to axial sliding movement of the inner tubular member toward the distal end of said outer tubular member.

15. An ophthalmic surgical apparatus as claimed in claim 14, wherein the distal end of said wire is curved in the direction of the distal side opening in the outer tubular member.

16. An ophthalmic surgical appartus as claimed in claim 14, wherein the distal end of the outer tubular member is closed by an end wall having a curved interior surface, and wherein said means for deflecting the distal end of the wire comprises said curved interior surface.

17. An ophthalmic surgical apparatus as claimed in claim 14, wherein said means for deflecting the distal end of the wire comprises a small diameter inner guide tube open at both ends and affixed within said outer tubular member in surrounding relationship with a portion of said wire.

18. In an ophthalmic surgical apparatus comprising a handpiece portion and an instrument portion, said instrument portion comprising rigid inner and outer tubular members with the inner tubular member axially slidable within the outer tubular member, and said handpiece portion comprising power-operated means for axially reciprocating said inner tubular member within said outer tubular member to produce a desired function at the instrument tip, the improved instrument portion comprising: an outer tubular member terminating a closed distal end immediately adjoining a distal side opening; an inner tubular member having an open distal end which terminates in a ribbon extension extending generally parallel to the longitudinal axis of said outer tubular member, said ribbon extension having its distal end positioned in proximity to the distal side opening in said outer tubular member, the distal end of said ribbon extension being formed with a single sharp distal tip adapted to form a discrete perforation in intraocular tissues; and means within the closed distal end of the outer tubular member for deflecting the distal end of said ribbon extension so that the sharp distal tip of said ribbon extension projects through said distal side opening at an angle relative to the longitudinal axis of the outer tubular member in response to axial sliding movement of the inner tubular member toward the distal end of said outer tubular member.

19. An ophthalmic surgical apparatus as claimed in claim 18, wherein the distal end of said ribbon extension is curved in the direction of the distal side opening in the outer tubular member.

20. An ophthalmic surgical apparatus as claimed in claim 18, further comprising a guide member affixed to the interior side wall of the outer tubular member at a position immediately behind the distal side opening therein, said guide member defining a narrow channel for guiding the movement of the ribbon extension in the vicinity of the distal side opening.

21. An ophthalmic surgical instrument as claimed in claim 20, wherein said guide member comprises a solid guide block, and wherein said channel is defined between an outer face of the guide block and the interior side wall of the outer tubular member.

22. An ophthalmic surgical instrument as claimed in claim 21, wherein said inner and outer tubular members are each circular in cross-section, and wherein said guide block comprises a solid cylinder with a narrow longitudinal section removed along one edge thereof.

23. An ophthalmic surgical instrument as claimed in claim 22, wherein said outer tubular member is provided with a second side opening spaced from said distal side opening and occupying a position between said guide member and the open distal end of said inner tubular member.

24. An ophthalmic surgical instrument as claimed in claim 23, wherein the distal end of the ribbon extension which extends beyond the channel defined by said guide member is curved in the direction of the distal side opening in the outer tubular member.

25. An ophthalmic surgical instrument comprising a rigid elongated outer tubular member terminating in a closed distal end immediately adjoining a distal side opening; a flexible elongated wire arranged within said outer tubular member and extending generally parallel to the longitudinal axis of said outer tubular member, said wire being axially movable within said outer tubular member and having a sharp distal end positioned in proximity to the distal side opening in said outer tubular member; and means within the closed distal end of the outer tubular member for deflecting the distal end of said wire so that said wire projects through said distal side opening at an angle relative to the longitudinal axis of the outer tubular member in response to axial movement of said wire toward the distal end of said outer tubular member, said deflecting means comprising a small diameter inner guide tube open at both ends and affixed within said outer tubular member in surrounding relationship with a portion of said wire, said inner guide tube being curved lengthwise through an arc of about 90° with one end positioned within the distal side opening in the outer tubular member and pointing in a direction approximately normal to the longitudinal axis of the outer tubular member, and with its opposite end positioned in the interior of the outer tubular member and pointing in a direction approximately parallel to the longitudinal axis of the outer tubular member.

26. An ophthalmic surgical instrument as claimed in claim 25, wherein said inner guide tube is affixed to the interior side wall of the outer tubular member.

27. In an ophthalmic surgical apparatus comprising a handpiece portion and an instrument portion, said instrument portion comprising rigid inner and outer tubular members with the inner tubular member axially slidable within the outer tubular member, and said handpiece portion comprising power-operated means for axially reciprocating said inner tubular member within said outer tubular member to produce a desired function at the instrument tip, the improved instrument portion comprising an outer tubular member terminating in a closed distal end immediately adjoining a distal side opening, an inner tubular member having an open distal end which terminates within said outer tubular member at a point behind said distal side opening, a flexible elongated wire arranged within said outer tubular member and carried by said inner tubular member, said wire extending generally parallel to the longitudinal axis of said outer tubular member and having a sharp distal end positioned in proximity to the distal side opening in said outer tubular member, and means within the closed distal end of the outer tubular member for deflecting the distal end of said wire so that said wire projects through said distal side opening at an angle relative to the longitudinal axis of the outer tubular member in response to axial sliding movement of the inner tubular member toward the distal end of said outer tubular member, said deflecting means comprising a small diameter inner guide tube open at both ends and affixed within said outer tubular member in surrounding relationship with a portion of said wire, said inner guide tube being curved lengthwise through an arc of about 90° with one end positioned within the distal side opening in the outer tubular member and pointing in a direction approximately normal to the longitudinal axis of the outer tubular member, and with its opposite end positioned in the interior of the outer tubular member and pointing in a direction approximately parallel to the longitudinal axis of the outer tubular member.

28. An ophthalmic surgical apparatus as claimed in claim 27, wherein said inner guide tube is affixed to the interior side wall of the outer tubular member.

* * * * *